United States Patent [19]

Sakai et al.

[11] Patent Number: 5,753,656
[45] Date of Patent: May 19, 1998

[54] METHOD FOR TREATING SPINOCEREBELLAR DEGENERATION

[75] Inventors: Tetsuo Sakai; Yasunobu Antoku; Toyojiro Matsuishi, all of Fukuoka-ken, Japan

[73] Assignee: Suntory Limited, Osaka, Japan

[21] Appl. No.: 632,412

[22] PCT Filed: Aug. 4, 1995

[86] PCT No.: PCT/JP95/01550

§ 371 Date: Apr. 3, 1996

§ 102(e) Date: Apr. 3, 1996

[87] PCT Pub. No.: WO96/03989

PCT Pub. Date: Feb. 15, 1996

[30] Foreign Application Priority Data

Aug. 5, 1994 [JP] Japan ................... 6-184682

[51] Int. Cl.$^6$ .................................................. A61K 31/495
[52] U.S. Cl. ........................................................... 514/249
[58] Field of Search ............................................. 514/249

[56] References Cited

U.S. PATENT DOCUMENTS

| 4,774,244 | 9/1988 | Curtius et al. | 514/249 |
| 4,920,122 | 4/1990 | Naruse et al. | 514/254 |

FOREIGN PATENT DOCUMENTS

| 59-25323 | 2/1984 | Japan . |
| 59-76086 | 4/1984 | Japan . |
| 61-277618 | 12/1986 | Japan . |
| 63-267781 | 11/1988 | Japan . |
| 9310155 | 5/1993 | WIPO . |

OTHER PUBLICATIONS

J. Pharmacol. Exp. Ther., 242(2), pp. 514–522, 1987.
Research Report by Medical Application Research Foundation, 12, pp. 233–240, 1994.

Sakai, Tetsuo, *Clinical Characteristics of Joseph Disease. A proposal of diagnostic criteria.*; 1989, pp. 216–252.

Mello, Karen et al., *Effects of Sulfamethoxazole and Trimethoprim on Neurologic Dysfunction in a Patient With Joseph's Disease*, Arch. Neurol., vol. 45, Feb. 1988, pp. 210–213.

*Primary Examiner*—Raymond Henley, III
*Attorney, Agent, or Firm*—Cushman Darby & Cushman IP Group of Pillsbury Madison & Sutro LLP

[57] ABSTRACT

The object of the present invention is to provide a therapeutic agent which effectively ameliorates neurologic symptoms in spinocerebellar degeneration. The present invention provides a therapeutic agent for spinocerebellar degeneration comprising as an effective ingredient a compound represented by the formula:

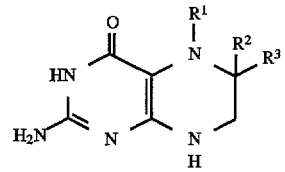

[wherein $R^1$ and $R^2$ each represents a hydrogen atom or, together, represent a single bond while $R^3$ represents —CH(OH)CH(OH)CH$_3$, —CH(OCOCH$_3$)CH(OCOCH$_3$)CH$_3$, —CH$_3$, —CH$_2$OH or a phenyl group when $R^1$ and $R^2$ each represents a hydrogen atom, or —COCH(OH)CH$_3$ when $R^1$ and $R^2$ together represent a single bond] or its pharmaceutically acceptable salt.

5 Claims, No Drawings

METHOD FOR TREATING SPINOCEREBELLAR DEGENERATION

This application is a 371 of international application PCT/JP95/01550 filed Aug. 4, 1995

BACKGROUND OF THE INVENTION

1. Field of Application in Industry

The present invention relates to an agent for treating spinocerebellar degeneration containing as an effective ingredient a compound represented by the formula (I):

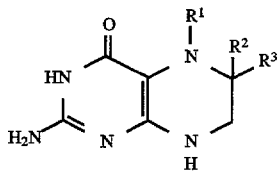

[wherein $R^1$ and $R^2$ each represents a hydrogen atom or, together, represent a single bond while $R^3$ represents —CH(OH)CH(OH)CH$_3$, —CH(OCOCH$_3$)CH(OCOCH$_3$)CH$_3$, —CH$_3$, —CH$_2$OH or a phenyl group when $R^1$ and $R^2$ each represents a hydrogen atom, or —COCH(OH)CH$_3$ when $R^1$ and $R^2$ together represent a single bond] or its pharmaceutically acceptable salt.

2. Prior Art

Spinocerebellar degeneration is a disease causing the degenerations of the nervous system mainly occurring in the cerebellar system, and can be roughly divided into non-hereditary and hereditary forms. The disease causes the systematic degeneration of the spinal cord, the cerebellum and its output and/or input pathway, and the cerebral basal ganglia with the subsequent attenuation of their neural functions. It is an intractable disease mainly characterized by the cerebellar ataxia, such as ataxic gait and tremor of the extremities, leading to manifestations of speech disturbance, dysphagia, abnormal ventilation and involuntary movements such as dystonia, thereby substantially interfering with activities of daily life. The cause of the disease remains unknown. With regard to its treatment, it has been reported that a marked improvement of neurologic symptoms was observed in a patient with Machado-Joseph disease, one of the spinocerebellar degeneration, following administration of a combined antimicrobial preparation of sulfamethoxazole-trimethoprim (hereinafter referred to as S-T preparation) (Archives of Neurology, 1988; 45: 210–213). Because of its serious side-effects, however, the drug has not been developed as therapeutic agent for administration to patients with this disease. Therefore, neither drugs for causal treatment nor those for symptomatic treatment of the disease which definitely provide an alleviation of symptoms, have as yet been established, and the advent of an effective therapeutic agent is keenly sought.

The effective ingredient, compound (I), of the therapeutic agent of the present invention is a known compound with proven clinical efficacy in the treatment of malignant hyperphenylalaninemia, depression, Parkinson disease, and other disorders. For example, refer to Japanese Patent Application Public Disclosure (KOKAI) Nos. 25323/84, 76086/84, 277618/86 and 267781/88.

SUMMARY OF THE INVENTION

The object of the present invention is to provide a safe therapeutic agent devoid of any side-effect, which reverses an attenuation of brain neural function with the consequent symptomatic amelioration, thus enabling the patient to lead a normal life.

In order to solve the above problem, the present inventors took note of the afore-mentioned improvement of neurologic symptoms observed following the administration of the antimicrobial agent S-T preparation in a patient with Machado-Joseph disease, one of the spinocerebellar degeneration (Archives of Neurology, 1988; 45: 210–213). Through an elaborate research into the mechanisms of pharmacologic actions of S-T preparation, the present inventors hypothesized that the drug produced improvement of neurologic symptoms by way of increasing the metabolic turnover rate in the brain tetrahydrobiopterin which is present in minute quantities in humans. In view of this, the inventors performed a clinical trial with tetrahydrobiopterin as the treatment of patients with Machado-Joseph disease. As a result, they discovered a remarkable amelioration of the neurologic symptoms to achieve the present invention. The present invention, relates to an agent for treating Machado-Joseph disease as well as other spinocerebellar degeneration having spinocerebellar lesion and pathology in common with Machado-Joseph disease.

DETAILED DESCRIPTION OF THE INVENTION

Therefore, the present invention is an agent for treating spinocerebellar degeneration comprising as an effective ingredient a compound represented by the formula (I):

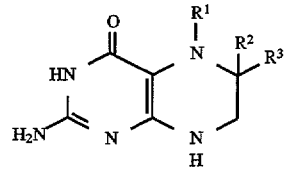

[wherein $R^1$ and $R^2$ each represents a hydrogen atom or, together, represent a single bond while $R^3$ represents —CH(OH)CH(OH)CH$_3$, —CH(OCOCH$_3$)CH(OCOCH$_3$)CH$_3$, —CH$_3$, —CH$_2$OH or a phenyl group when $R^1$ and $R^2$ each represents a hydrogen atom, or —COCH(OH)CH$_3$ when $R^1$ and $R^2$ together represent a single bond] or its salt.

Specific compounds represented by formula (I), which is the effective ingredient of this invention, include the following and their salts:

(6R)-L-Erythro-5, 6, 7, 8-tetrahydrobiopterin
(hereinafter referred to as BH4)

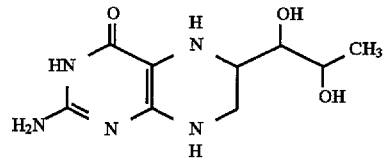

(6R, S)-5, 6, 7, 8-Tetrahydrobiopterin
1', 2'-Diacetyl-5, 6, 7, 8-tetrahydrobiopterin

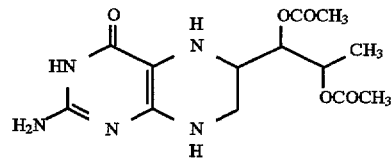

Sepiapterin

-continued

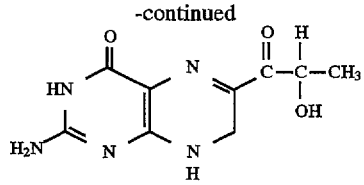

6-Methyl-5, 6, 7, 8-tetrahydropterin

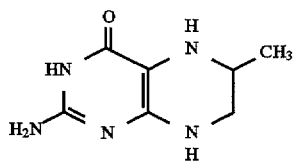

6-Phenyl-5, 6, 7, 8-tetrahydropterin

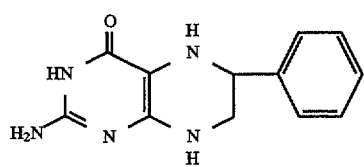

Of the above compounds, preferred compounds are 5,6,7,8-tetrahydrobiopterins and their salts, among which the most preferred one is BH4 or its salt.

The compounds represented by formula (I), the effective ingredient of this invention, are known compounds. In this regard, for example, Japanese Patent Application Public Disclosure (KOKAI) Nos. 25323/84, 76086/84, 277618/86 and 267781/88 may be referred to. These compounds may be used in the form of appropriate salts, and, as examples of such salts, those with pharmacologically nontoxic acids, e.g. inorganic acids such as hydrochloric acid, phosphoric acid, sulfuric acid and boric acid, and organic acids such as acetic acid, formic acid, maleic acid, fumaric acid and methanesulfonic acid, may be included.

In the present specification, the term "spinocerebellar degeneration" means a disease causing the degenerations of the nervous system mainly in the cerebellar system, and a pathology which develops cerebellar ataxia as a major symptom. As mentioned above, spinocerebellar degeneration can be divided into non-hereditary and hereditary forms. Both forms show systematic degeneration of the spinal cord, the cerebellum and its output and/or input pathway, and the cerebral basal ganglia with the consequent gradual attenuation of neural functions. The disease is mainly characterized by cerebellar ataxia, such as ataxic gait and tremor of the extremities, followed by manifestations of speech disturbance, dysphagia, abnormal ventilation and involuntary movements such as dystonia.

Non-hereditary spinocerebellar degeneration includes Shy-Drager syndrome, olivo-ponto-cerebellar atrophy (Dejerine-Thomas type), striatonigral degeneration, and late cortical cerebellar degeneration.

Hereditary spinocerebellar degeneration includes autosomal dominant one and autosomal recessive one. Autosomal dominant spinocerebellar degeneration denotes all those diseases controlled by a dominant gene situated at its locus on an autosome and its representatives are Machado-Joseph disease (the genetic locus on chromosome 14q), SCA1 (the locus on chromosome 6p), SCA2 (the locus on chromosome 12q), hereditary cerebellar cortical atrophy (Holmes type), dentato-rubro-pallido-luysian atrophy (DRPLA) (the locus on chromosome 12p) and hereditary spastic paraplegia. It has also become recognized that virtually all cases [with the previous diagnosis of hereditary olivo-ponto-cerebellar atrophy (OPCA) or Menzel type OPCA] belong to this group of spinocerebellar degeneration. Autosomal recessive spinocerebellar degeneration denotes all those diseases controlled by a recessive gene situated at its locus on an autosome, and its representatives are Friedreich ataxia (the locus on chromosome 9q13–q21) and others.

These disease present similar pathologic features and the cerebellum and other surrounding regions have similarly degenerated though varying in extent and/or severity.

In this patent specification, the invention will be described hereunder with 'Machado-Joseph disease' as a typical example of spinocerebellar degeneration, which is the most common among autosomal dominant spinocerebellar degeneration. Machado-Joseph disease presents the cerebellar lesion and pathology in common with other hereditary and non-hereditary spinocerebellar degeneration such as SCA1, SCA2 or the like, and therefore, this example supports the effects of the compound represented by the formula (I) to these diseases. Machado-Joseph disease is mainly characterized by cerebellar ataxia and pyramidal signs, and is generally classified into three types, i.e. types 1 to 3, according to clinical features of the disease (Sakai, T.: Neurological Medicine, 30: 246–252, 1989). Diagnostic criteria for the disease have also been proposed by T. Sakai (ibid., pp. 249–251) and is adopted in the description of treated cases in this specification.

The therapeutic agent of the present invention is prepared by providing the compound of formula (I) in dosage form suitable for oral, intrarectal or parenteral (including intravenous and intrathecal) administration, together with a carrier or carriers in common pharmaceutical use by a conventional method.

As the carriers used in these pharmaceutical preparations, generally excipients, binders and disintegrators may be mentioned though depending upon the dosage form intended.

Typical examples of the excipients include starch, lactose, sucrose, glucose, mannitol, and cellulose; and those of the binders include polyvinylpyrrolidone, starch, sucrose, hydroxypropyl cellulose, and Arabic gum. As examples of the disintegrators, starch, agar, gelatin powder, cellulose, and CMC can be mentioned. Other substances may also be used insofar as they are excipients, binders and disintegrators in common use.

The therapeutic agent of the present invention will preferably contain an antioxidant in addition to the above carriers, in order to stabilize the effective ingredient. Such antioxidant can be selected appropriately from those commonly used in pharmaceutical preparations, e.g. ascorbic acid, N-acetylcysteine, L-cysteine, dl-α-tocopherol, and natural tocopherol. The amount of the antioxidant to be used may be such that it suffices for stabilization of the active ingredient (one or more) and, generally, is preferably between 0.2 and 2.0 parts by weight to 1 part of the active ingredient.

The pharmaceutical preparation of this invention suitable for oral administration may be made available in the form of tablets, capsules, powder, trituration or granules as well as in the form of suspension in non-aqueous liquid such as syrup, emulsion or draft (pro re nata preparation) that contains the prescribed amount of the active ingredient (one or more).

The granules may be provided by homogeneously mixing the active ingredient (one or more) with one or more adjuvants such as the above carriers and antioxidants, and subsequently granulating and sieving to a uniform grain size. The tablets can be prepared by compressing or molding the active ingredient (one or more) together with one or more adjuvants as required. The capsules are prepared by homogeneously mixing the active ingredient (one or more) with one or more adjuvants as required and by filling the resulting powder mixture or granules into suitable capsules by means of capsule filling machine or by other means. The preparation for intrarectal administration may be provided in the form of suppositories using conventionally used carriers such as cacao butter. The preparation for parenteral administration can be provided as a dry (lyophilized) solid of the active ingredient (one or more) sealed in sterilized, nitrogen-cleansed containers. The dry (lyophilized) solid preparation may be dispersed or dissolved in a prescribed volume of sterile water just prior to parenteral administration to a patient.

In manufacturing these pharmaceutical preparations, it is preferable to formulate the drug by adding the above antioxidant to the active ingredient and common carriers and, if desired, by further supplementing it with one or more adjuvants selected from buffers, flavoring agents, surfactants, viscosants, or lubricants.

The dose of the active ingredient, i.e. the compound of formula (I), varies, of course, with the course of administration, with the symptom to be treated and with the patient being treated, but ultimately should be left at the discretion of the physician.

Appropriate dosage of the subject agent for treating spinocerebellar degeneration is between 0.1 and 50 mg/kg (b.w.)/day and representative optimal dosage is 0.5–10 mg/kg (b.w.)/day.

A desired dosage of the said active ingredient may be administered once a day or in two to four divided doses a day at appropriate intervals.

The active ingredient may be administered alone as it is without mixing with other ingredients, but may preferably be administered in the form of pharmaceutical preparation of the active ingredient for reasons of facilitating dosage adjustment, and so forth.

The pharmaceutical preparation of this invention may contain at least one adjunctive active ingredient selected from the group consisting of tryptophan, 5-hydroxytryptophan (5-HTP), tyrosine and L-DOPA, together with the compound of formula (I) as active ingredients. A greater therapeutic efficacy for spinocerebellar degeneration can generally be expected with such combination of active ingredients, compared to the use of the compound of formula (I) alone. The proportion of the said individual ingredient in the pharmaceutical preparation of this invention is not particularly limited, but, for example, may be within a range of 0.1 to 10 parts by weight of at least one selected from the group consisting of tryptophan, 5-HTP, tyrosine and L-DOPA, preferably within a range of 0.5–2 parts, to 1 part of the compound of formula (I).

Adequate dosage of this combined preparation in the treatment of spinocerebellar degeneration, in terms of total amount of the combined active ingredients, is 0.1–50 mg/kg (b.w.)/day, preferably 0.5–10 mg/kg(b.w.)/day.

In clinical practice of the treatment, the issue is left at the discretion of the physician which pharmaceutical preparation is to be selected, those containing the compound of formula (I) alone as the active ingredient, or those containing it in combination with other active ingredient(s), depending on the age, the symptom or the like.

As the active ingredients provided by the present invention for treatment of spinocerebellar degeneration, (6R)-L-erythro-5,6,7,8-tetrahydrobiopterin (BH4) and its salts are most preferable, but analogous compounds such as (6R,S)-5,6,7,8-tetrahydrobiopterin, 1',2'-diacetyl-5, 6,7,8-tetrahydrobiopterin, sepiapterin, 6-methyl-5,6,7,8-tetrahydropterin or 6-phenyl-5,6,7,8-tetrahydropterin and their salts may also be acceptable. However, needless to say, BH4 which naturally exists in the body is preferable. Acute oral toxicity of BH4 dihydrochloride, in terms of $LD_{50}$, in rats is more than 2 g/kg; hence practically non-toxic. (6R, S)-5,6,7,8-tetrahydrobiopterin, an optically inactive analogue, is also only slightly toxic as seen in the treatment of patients with Parkinson disease which is described in Japanese Patent Application Public Disclosure (KOKAI) No. 25323/84 and can be used for treating spinocerebellar degeneration. The other compounds belonging to formula (I) likewise have little or no acute toxicity.

The present invention will now be further illustrated by the following examples. This invention, of course, should not be limited to the following examples.

EXAMPLES

Example 1 (Granules and fine granules)

One part (by weight) of polyvinylpyrrolidone (Kollidon 30) was dissolved in sterile purified water, and, to the resultant solution, 10 parts of ascorbic acid and 5 parts of L-cysteine hydrochloride were added to obtain a homogeneous solution. To this solution, 10 parts of BH4 dihydrochloride were added to prepare a homogeneous solution.

The solution was added to a mixture of 59 parts of an excipient (mannitol or lactose) and 15 parts of a disintegrator [corn starch or hydroxypropyl cellulose (LH-22)], kneaded, granulated, then dried, and sieved.

Example 2 (Tablets)

To the homogeneous solution of the active ingredient prepared in Example 1, 58 parts of lactose and 15 parts of microcrystalline cellulose were added and mixed, then one part of magnesium stearate was added, and the resultant mixture was compressed into tablets.

Example 3 (Capsules)

The dosage form prepared in Example 1 was filled in capsules, wherein the formulation included 0.2% of magnesium stearate as a lubricant.

Example 4 (Injection)

| BH4 dihydrochloride | 1.5 g |
| Ascorbic acid | 1.5 g |
| L-Cysteine hydrochloride | 0.5 g |
| Mannitol | 1.5 g |

The above ingredients were dissolved in sterile purified water sufficient to make 100 ml, then sterilized by filtration, dispensed in 1- or 2-ml aliquots into vials or ampules, lyophilized, and sealed.

Example 5 (Injection)

2.0 g of BH4 dihydrochloride were dissolved in sterile purified water sufficient to make 100 ml under an anaerobic atmosphere, then sterilized by filtration, dispensed, and sealed in the same manner as in Example 4.

Example 6 (Suppositories)

| | |
|---|---|
| BH4 dihydrochloride | 150 parts |
| Ascorbic acid | 150 parts |
| L-Cysteine hydrochloride | 50 parts |

A homogeneous powder made of a mixture of the above ingredients was dispersed in 9950 parts of cacao butter.

Example 7 (Granules)

| | |
|---|---|
| BH4 dihydrochloride | 5 parts |
| Ascorbic acid | 5 parts |
| L-Cysteine hydrochloride | 2 parts |

A homogeneous solution was prepared with the above ingredients.

The solution was then added to a homogeneous mixture of 55 parts of mannitol, 1 part of polyvinylpyrrolidone, 14 parts of hydroxypropyl cellulose and 5 parts of 5-HTP, kneaded, granulated, dried, and sieved.

Example 8 (Granules)

| | |
|---|---|
| BH4 dihydrochloride | 5 parts |
| Ascorbic acid | 5 parts |
| L-Cysteine hydrochloride | 5 parts |
| Mannitol | 52 parts |
| Polyvinylpyrrolidone (Kollidon 30) | 1 part |
| Hydroxypropyl cellulose (LH-22) | 12 parts |
| L-DOPA | 10 parts |

The above ingredients were processed, granulated, and sieved in the same manner as in Example 7, but using 10 parts of L-DOPA in place of the 5 parts of 5-HTP.

Example 9 (Granules)

| | |
|---|---|
| BH4 dihydrochloride | 5 parts |
| Ascorbic acid | 5 parts |
| L-Cysteine hydrochloride | 2 parts |

A homogeneous solution of the above ingredients was prepared.

The solution was then added to a homogeneous mixture of 5 parts of 5-HTP, 10 parts of L-DOPA, 50 parts of mannitol, 1 part of polyvinylpyrrolidone (Kollidon 30) and 9 parts of hydroxypropyl cellulose (LH-22), kneaded, granulated, dried and sieved.

Though not constrained by theory, the propriety of therapy with the compound of formula (I) based on biochemical considerations is illustrated as follows.

Taking note of the report documenting a marked improvement of neurologic symptoms observed following administration of a combined antimicrobial sulfamethoxazole-trimethoprim preparation (hereinafter referred to as S-T preparation) in a patient with Machado-Joseph disease (Archives of Neurology, 1988; 45: 210–213), the present inventors made the following hypothesis, on the grounds that there is no enzyme upon which sulfamethoxazole acts in humans whereas an enzyme upon which trimethoprim acts does exist in humans, that trimethoprim inhibits the activity of dihydrofolic acid reductase (DHFR) via competitive inhibition against dihydrofolic acid, that DHFR is homologous to dihydropteridine reductase (DHPR), and therefore that trimethoprim might possibly inhibit not only DHFR but DHPR as well. "In patients prior to treatment with S-T preparation, the BH4 level in brain tissue is markedly diminished due to degeneration not only of nigrostriatal neurons containing BH4 but also of cerebellar neurons containing BH4. As a result, tissue levels of phenylalanine hydroxylase, tyrosine hydroxylase and tryptophan hydroxylase activity are decreased and, consequently, those of catecholamines and serotonin arising from the hydroxylation reactions thereof are also lowered in the patients Following treatment with S-T preparation, DHPR activity in brain tissue is inhibited, which, in turn, leads to lowering of BH4 regeneration. This eventually stimulates the BH4 biosynthetic-metabolic system with a consequent increase in metabolic turnover rate of BH4 biosynthesis in the brain, resulting in elevation of tissue levels of the said three amino acid hydroxylase activity and thus in increased tissue catecholamine and serotonin concentration. Furthermore, it has recently been demonstrated that BH4 plays an important role, as a coenzyme, in the activity of nitric oxide synthase abundant in the cerebellum. The increase in metabolic turnover rate of BH4 would possibly contribute also to an increase in nitric oxide synthesis in the cerebellar neurons. The clinical ameriolation of cerebellar symptoms, psychic symptoms and dystonia in Machado-Joseph disease can be explained by these effects of the drug."

(Preliminary study)

Eight patients with Machado-Joseph disease were administered S-T preparation and a placebo (lactose) for four weeks each (with a two-week washout period between the treatments) and were assessed by neurological examinations in each of the treatment periods [by a double-blind, placebo-controlled crossover design]. The patients were observed to ascertain whether the treatment with S-T preparation might afford improvement of neurologic symptoms or not. Concurrently, blood and cerebrospinal fluid samples obtained immediately before the start and on the last day of each of the S-T preparation treatment period and the placebo treatment period were assayed for total biopterin, and oxidized and reduced forms of biopterin, homovanillic acid (HVA) and 5-hydroxyindoleacetic acid (HIAA). The results were presented as below.

1. Clinical study:

Clinically, a statistically significant improvement was noted during the S-T preparation treatment period as assessed in respect of the following eight test parameters:

① Disturbance of gait ($p<0.05$)
② Finger-to-nose test (right hand; $p<0.02$)
③ Finger-tapping test (left hand; $p<0.05$)
④ Diadochokinetic test
   (right hand, $p<0.01$; left hand, $p<0.05$)
⑤ Heel-to-knee tapping test
   (right leg, $p<0.02$; left leg, $p<0.05$)
⑥ "PaTa" repetition test ($p<0.05$)
⑦ Dial Telephone ($p<0.05$)
⑧ Slotted can ($p<0.01$)

2. Biochemical study to clarify the mechanisms of pharmacological actions (1) Before treatment with S-T preparation:

Total biopterin, oxidized and reduced biopterin concentrations in cerebrospinal fluid (CSF) of the patients with Machado-Joseph disease were found to be reduced to less than half the values in the diseased control group (7 cases of progressive muscular dystrophy and 1 case of Sjogren syndrome). CSF levels of HVA in the Machado-Joseph disease patient group were also found to be reduced to less than half of those in the diseased control group.

(2) After treatment with S-T preparation.

The total biopterin and oxidized biopterin concentrations in CSF showed a significant increase (to 133 and 172% of the pre-treatment levels, respectively) while the CSF level of reduced biopterin did not show any significant increase. Since these changes in CSF biopterin concentration were characteristic, in pattern, solely of dihydropteridine reductase (DHPR) defect, one of the three known forms in the inherited metabolic diseases of BH4, the above findings provided an indirect evidence to support the hypothesis made by the present inventors that S-T preparation would inhibit DHPR activity in the brain of the patients with Machado-Joseph disease. These findings, together with a concurrent significant increase in relative HVA and HIAA values in CSF observed in response to the administration of S-T preparation, suggest that the inhibition of DHPR activity brought about by S-T preparation might give rise to an increase in metabolic turnover rate in brain BH4 biosynthesis via a facilitative feedback to the BH4 biosynthetic-metabolic pathway, thus resulting in increased synthesis of catecholamines and serotonin in the brain.

From the results of this preliminary study, the mechanism whereby S-T preparation ameliorated neurologic symptoms in the patients with Machado-Joseph disease is assumed to be that trimethoprim should increase the metabolic turnover rate of BH4 the level of which might probably be markedly reduced in the brain. Based on the conception, therefore, that administration of BH4 itself should be rational, the BH4 therapy was performed in patients with Machado-Joseph disease and a remarkable therapeutic efficacy was obtained.

(Therapeutic Example)

To 5 patients with Machado-Joseph disease listed in Table 1, a placebo (ascorbic acid) and BH4 were administered in a double-blind clinical trial with the procedure as follows:
<Subjects and Methods>
1. Subjects Three patients from three families diagnosed as "clinically definite family" and two patients from two families diagnosed as "probable family" according to the diagnostic criteria by Sakai (Sakai, T., ditto) were selected. Neurological findings in individual patients are summarized in Table 1.

TABLE 1

Statistical data on five patients with Machado-Joseph disease

| Case No. | 1 | 2 | 3 | 4 | 5 |
|---|---|---|---|---|---|
| Age/sex | 40/M | 42/M | 45/M | 51/M | 56/M |
| Duration of illness (yr) | 19 | 6 | 16 | 6 | 12 |
| Type of disease | 1 | 2 | 1 | 2 | 2 |
| Sakai's diagnostic criteria | probable | definite | definite | definite | probable |
| Neurological findings | | | | | |
| Cerebellar signs | + | + | + | + | + |
| Pyramidal signs | + | + | + | + | + |
| Extrapyramidal signs | ++ | − | ++ | − | ± |
| Muscular atrophy | + | − | + | − | − |
| Whether or not any concurrent drug acting on CNS* | + | − | + | − | + |

*These drug medications remained uninterrupted in dosage or type since at least one month prior to the start of and throughout the double-blind trial.

2. Treatment period

The patients received BH4 and a placebo (ascorbic acid) for 10 consecutive days each, with a washout period of 9 days between them, hence a total study period of 29 days.

3. Dosage

The patients received 1 mg/kg(b.w.) of BH4 or ascorbic acid in capsules once daily, after lunch. The chemical form of BH4 given was BH4 dihydrochloride in Cases 1 to 3 and 5 and (6R,S)-L-erythro-5, 6,7,8-tetrahydrobiopterin dihydrochloride in Case 4.

4. Evaluation methods

Each patient was assessed by the following three methods:

a. Subjective improvement

Each patient was asked with respect to six symptomatic parameters: dysarthria, dysphagia, disturbance of dexterity, disturbance of stationary balance on standing, disturbance of gait, and overall sense of general well-being.

b. Neurological examination

The examination was performed in respect of muscle tonus of the extremities, deep reflexes, severity of dystonia, disturbance of stationary balance on standing, finger-to-nose test, finger tapping test, diadochokinetic test, heel-to-knee tapping test, and dysarthria.

c. Timed tests

Finger-to-nose test, finger tapping test, diadochokinetic text, heel-to-knee tapping test, Pa/Pata repetition test, and measurements of times required to execute a 10-meter walk, dial telephone and slotted can.

5. Study design

A double-blind, placebo-controlled crossover design was adopted.

6. Statistical analysis

Data were analyzed using paired t-test.

<Results>

1. Subjective symptoms

Of the subjective symptoms assessed, none showed a statistically significant improvement while dysphagia tended to be ameliorated on day 1 of BH4 administration ($p < 0.10$).

2. Objective findings (1) Neurological checkup

Of the neurological parameters assessed, none exhibited a statistically significant improvement while exaggerated knee jerks tended to be ameliorated on day 10 of BH4 administration ($p < 0.10$)

(2) Timed tests

The following test parameters revealed a statistically significant improvement during the BH4 administration period.

①  Finger-to-nose test (right hand):
Day 3 ($p < 0.02$), day 4 ($p < 0.05$) and day 10 ($p < 0.05$) of administration ②  Finger-tapping test (left hand):
Day 8 of administration ($p < 0.02$)

③  Diadochokinetic test (right hand):
Day 5 of administration ($p < 0.05$)

④  Dial telephone:
Day 4 of administration ($p < 0.05$)

In addition to the above, a tendency to improvement was noted in respect of:

①  Diadochokinetic test (left hand):
Day 4 of administration ($p < 0.10$)

②  Slotted can:
Day 5 of administration ($p < 0.10$)

<Conclusion>

From the above results of assessments of subjective symptoms and objective findings, it is concluded that BH4 proved to be effective in improving neurologic symptoms of Machado-Joseph disease.

As illustrated above, the present invention provides a therapeutic agent which effectively ameliorates neurologic symptoms in an intractable disease, spinocerebellar degeneration.

We claim:

1. A method of treating spinocerebellar degeneration in a patient suffering from spinocerebellar degeneration by administering to the patient a therapeutically effective amount of a compound represented by the formula:

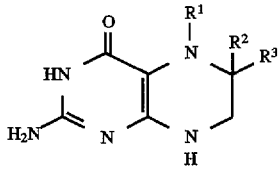

wherein $R^1$ and $R^2$ each represents a hydrogen atom or, together, represent a single bond while $R^3$ represents —CH(OH)CH(OH)CH$_3$, —CH(OCOCH$_3$)CH(OCOCH$_3$)CH$_3$, —CH$_3$, —CH$_2$OH or a phenyl group when $R^1$ and $R^2$ each represents a hydrogen atom, or —COCH(OH)CH$_3$ when $R^1$ and $R^2$ together represent a single bond or its salt.

2. The method of treating spinocerebellar degeneration according to claim 1, wherein $R^3$ is L-erythro-CH(OH)CH(OH)CH$_3$.

3. The method of treating spinocerebellar degeneration according to claim 1 which ameliorates neurological symptoms in spinocerebellar degeneration.

4. The method of treating spinocerebellar degeneration according to claim 1, wherein spinocerebellar degeneration is an autosomal dominant spinocerebellar degeneration.

5. The method of treating spinocerebellar degeneration according to claim 1, wherein spinocerebellar degeneration is Machado-Joseph disease.

* * * * *